United States Patent [19]

Fischell

[11] Patent Number: 4,494,950

[45] Date of Patent: Jan. 22, 1985

[54] PLURAL MODULE MEDICATION DELIVERY SYSTEM

[75] Inventor: Robert E. Fischell, Silver Spring, Md.

[73] Assignee: The Johns Hopkins University, Baltimore, Md.

[21] Appl. No.: 340,817

[22] Filed: Jan. 19, 1982

[51] Int. Cl.³ .................................................. A61M 5/00
[52] U.S. Cl. ..................................... 604/66; 128/635; 128/903
[58] Field of Search ............... 128/631, 635, 696, 903; 604/65–67, 897

[56] References Cited

U.S. PATENT DOCUMENTS

| | | | |
|---|---|---|---|
| 3,212,496 | 10/1965 | Preston | 128/903 |
| 3,253,588 | 5/1966 | Vuilleumier et al. | 128/903 |
| 3,757,770 | 9/1973 | Brayshaw et al. | 128/631 |
| 3,800,801 | 4/1974 | Gaillard | 128/419 PT |
| 3,837,339 | 9/1974 | Aisenberg et al. | 128/903 |
| 4,041,954 | 8/1977 | Ohara | 128/419 PT |
| 4,146,029 | 3/1979 | Ellinwood, Jr. | 604/891 |

Primary Examiner—William E. Kamm
Attorney, Agent, or Firm—Robert E. Archibald; Howard W. Califano

[57] ABSTRACT

A system consisting of a multiplicity of separate modules which collectively perform a useful biomedical purpose; the modules communicating with each other without the use of interconnecting wires. All modules may be intracorporeal or body mounted extracorporeal or some modules may be intracorporeal with others being body mounted extracorporeal. Signals are sent from one module to another by electromagnetic waves, by electrical signals using the body as an electrical conductor, or by acoustic waves. Physiologic sensor measurements sent from a first module causes a second module to perform some function in a closed-loop manner. One extracorporeal module can provide electrical power to an intracorporeal module; which power operates means for transferring data from the intracorporeal module to the body mounted extracorporeal module.

6 Claims, 4 Drawing Figures

PLURAL MODULE MEDICATION DELIVERY SYSTEM

FIELD OF THE INVENTION

The present invention relates to systems of biomedical devices that have two or more modules both or all of which may be implanted in the body of a human or animal (i.e. all modules are intracorporeal), or systems having one or more intracorporeal module(s) with one or more body mounted extracorporeal module(s), or systems that have both or all modules located extracorporeally onto the body. The present invention has utility in various applications requiring remote communication between such modules (i.e. without the use of interconnecting wires).

In general, the word "extracorporeal" refers to anything external to the skin of a body. However, as used herein, the word "extracorporeal" is defined in a more restricted sense; namely, it refers to biomedical devices (or modules) that are external to the body, but are also mounted directly onto the patient's body, that is, are body mounted and therefore are actually being carried by the patient. Furthermore, the usage of extracorporeal modules are described herein is further limited to those uses that are substantially continuous, i.e., for at least many hours each day. An external programming module to reprogram an implantable pacemaker is an example of one module being intracorporeal (the pacemaker) and the other module (the programming module) being outside the body. This is not the class of systems described herein because:

(1) The communication module is typically not mounted onto the body, and (2) The communication module would typically be used only a few minutes each year and certainly not many hours each day.

The term "body mounted", as used herein, is defined as mounted on the patient's skin or mounted on or carried in the patient's clothing.

A case of two modules, both of which are implanted, might be a blood glucose sensor located on the inside wall of a major vein that sends out electromagnetic signals whose frequency is proportional to blood glucose levels to a remotely located implantable medication release system that infuses insulin into the body to control the blood sugar in a closed-loop manner.

One example of a case with one module extracorporeal and the other implanted is for the external module to consist of a glucose sensor on the skin or placed in a needle tip just below the skin that measures blood glucose and transmits a signal frequency into an implanted medication release system which frequency is proportional to the level of blood sugar so that an appropriate rate of insulin might be infused into the body from an implanted medication release module in a closed-loop manner. This system has the advantage that the essentially extracorporeal sensor can be frequently replaced.

An example of a case with both modules extracorporeal is a copending application by R. E. Fischell, G. H. Fountain and C. M. Blackburn entitled "Self-Injurious Behavior Inhibiting System" (SIBIS), filed of even date herewith and having a common assignee with the present application. In this copending application, one module with an accelerometer detects some portion of the body being struck which causes an electrical signal to be sent to another module mounted extracorporeally on the body that produces an aversive electrical shock in an effort to condition the patient against self-injurious behavior.

Although the principle use of such systems will be with humans, it is also applicable to any living being, for example domestic animals. Furthermore, communication between a multiplicity of devices (i.e. more than two) is also envisioned.

REFERENCE TO RELATED CASE

One novel application of the present invention, involving two or more extracorporeal modules, is disclosed in a copending patent application entitled "Self-Injurious Behavior Inhibiting System", filed of even date herewith, by R. E. Fischell, G. H. Fountain and C. M. Blackburn and having a common assignee with the present application.

TECHNOLOGICAL CONTENT AND BACKGROUND OF THE INVENTION

In U.S. Pat. No. 4,146,029, Ellinwood suggests a large variety of physiologic sensors all connected by wires to an implanted means for infusing medication. For a variety of reasons, it may not be practical or convenient to connect wires to such sensors. It may not be desirable or practical to connect wires to some implanted sensor (which sensor constitutes one implanted module) because the wires may be damaging to the body, less reliable or may in fact disturb the physiologic measurement.

An article entitled "Long-Term Perfect Glycemic Control With Wearable Artificial Endocrine Pancreas in Depancreatized Dogs", by M. Schichiri et al, at Osaka University Medical School was published in the *Abstracts of the International Symposium on Artificial Systems for Insulin Delivery*, Assisi, Italy, Sept. 20–23, 1981. This article relates that a glucose sensor, located on the tip of a needle just below the skin attached to an extracorporeal module, was able to accurately measure blood glucose for as long as 7 days. However, Schichiri et al anticipate that the signal from the needle blood glucose sensor will be delivered by an electrical wire to an external pump that delivers insulin. It may, however, be much more advantageous to send a signal from an essentially extracorporeal module (except that the needle sensor is actually beneath the skin) to an implanted insulin release system which could then regulate blood glucose in a closed-loop manner. This system has the advantage that the insulin release system is beneath the skin while the glucose sensor module, being extracorporeal and known to have a limited lifetime, can be readily replaced. An important advantage of the system is that the external portions of the system can be removed during sleep, with the implantable insulin release system going into an open-loop mode to deliver basal insulin during sleep.

In U.S. Pat. No. 3,834,379, entitled "Deterrent for Self-Destructive Actions," Grant suggests a biomedical device system consisting of two extracorporeal modules connected to each other by electrical wires. Described in the Grant invention is one module on the head that senses when the head is struck and another module on the arm that applies an electrical shock for the purpose of conditioning the patient to cease striking his head. The use of electrical wires to interconnect these two extracorporeal modules is disadvantageous because they significantly decrease the reliability of the system, as a result of the fact that the wires get caught on objects and therefore become broken and because such wires are awkward to mount on a patient for extended periods of time. By means of the invention described herein and the system disclosed in the copending Fischell et al application, aversive electrical stimulation to inhibit self-injurious impacts can be accomplished with two extracorporeal modules and without the use of interconnecting wires.

More particularly, in the copending Fischell et al application, an extracorporeal sensing module (typically on the head) senses if that portion of the body is struck. If struck, the sensing module causes a signal to be sent to a remote extracorporeal stimulation module, that produces an aversive electrical shock. The copending Fischell et al application also teaches the use of a multiplicity of extracorporeal sensing modules (e.g. one on the head and one each on each knee and elbow) communicating with an extracorporeal aversive stimulation module. In accordance with the present invention, the sensed signal could, as well, be transmitted to an intracorporeal stimulation module that could be a very effective aversive stimulator by applying an electrical signal directly to a nerve. The present invention furthermore extends beyond the teaching of the copending application by contemplating a multiplicity of intracorporeal modules communicating with each other and/or with a multiplicity of extracorporeal modules.

Although it is well known to have an external programmer communicate with an intracorporeal module, as is the case with cardiac pacemakers that have command and telemetry systems, such external programmers are not carried on the patient who has the implanted pacemaker. The present invention teaches extracorporeal modules that are mounted onto the patient and are in more or less continuing communication with other intra- or extracorporeal modules.

DESCRIPTION OF THE INVENTION

Figure 1:
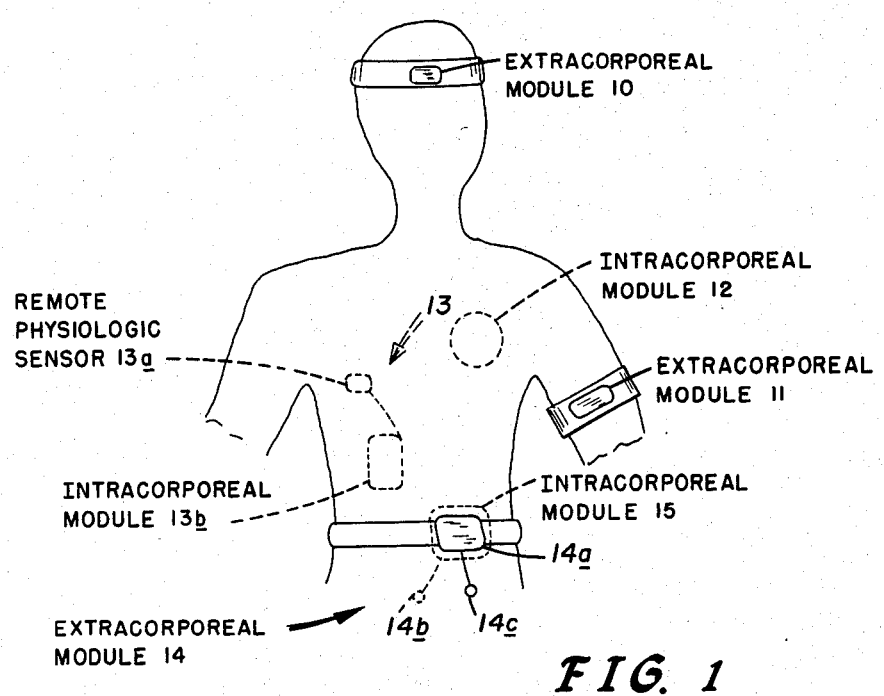
FIG. 1 is a diagrammatic illustration of the general system embodying the present invention and including a multiplicity of intercommunicating intracorporeal and extracorporeal modules.

In FIG. 1 is shown several examples of biomedical device systems consisting of several modules, any one of which could be intra- or extracorporeal. In FIG. 1, an extracorporeal module 10 on the patient's head might communicate with extracorporeal module 11, as described in the copending Fischell et al application, or it might communicate with intracorporeal module 12. The communication between these remotely located modules might be by electrical signals conducted through the body, by electromagnetic waves which may be partially or entirely transmitted through the air or by acoustic (e.g. ultrasonic) signals.

A remote, implanted physiologic sensor 13a (e.g. a glucose sensor) is connected by a wire to a transmitter unit 13b and together form an intracorporeal module 13, as shown in FIG. 1. This module 13 might communicate with any of the other extracorporeal modules 10, 11, or 14 or with intracorporeal modules 12 or 15 shown in FIG. 1. The details of intracorporeal module 13 will be described hereinafter, with reference to FIG. 2.

Another class of communicating modules is shown in FIG. 1 as intracorporeal module 15 which is associated with the extracorporeal module 14. For this case, the two communicating modules have been deliberately placed in close proximity to each other. The module 14 might be placed on a belt, with the module 15 being implanted subcutaneously in the abdominal region. The module 14 might be in the form of a decorative belt buckle. In this configuration, communication between the modules 14 and 15 would be improved because of the close proximity, but also module 14 would be able to provide electrical power to module 15 by means of magnetic induction.

The module 14, could also receive communication from other extracorporeal modules such as module 10 and, module 11. In addition to receiving signals from module 15, module 14 could receive signals from other intracorporeal modules such as module 12 and module 13.

Figure 2:
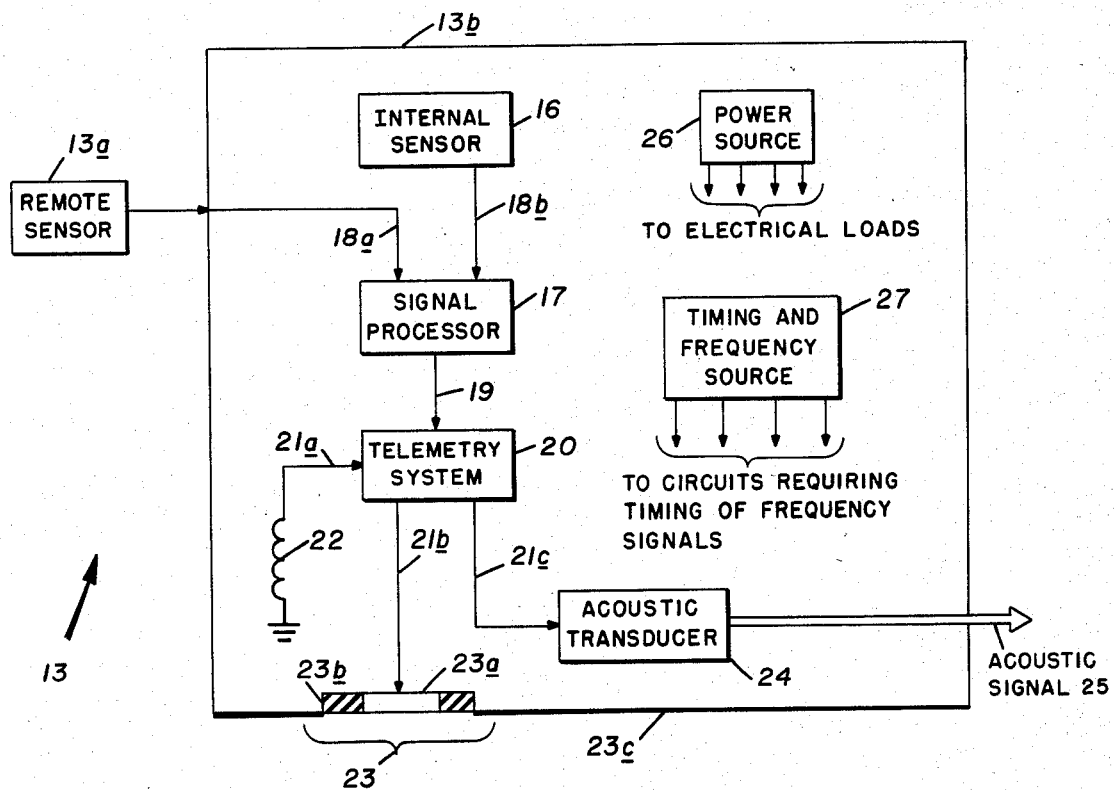
FIG. 2 is a block diagram of a typical intracorporeal module, proposed in accordance with one embodiment of the present invention, for transmitting through the user's body an acoustic signal, electrical signal, and/or electromagnetic signal.

FIG. 2 shows a typical transmitting module which could be used to collect (but not necessarily store) data and send it to a receiving module. For example, let us say that the intracorporeal module 13 of FIG. 1 is such a transmitting module. From FIG. 2 we see that module 13 has two separate portions, a remote sensor 13a and a transmitter unit 13b which together constitute the intracorporeal transmitting module 13. Module 13 might also have an internal sensor 16 such as one to measure temperature or acceleration. A signal processor, 17 has two input lines, 18a and 18b from the remote sensor 13a and the internal sensor 16 respectively. The signal processor 17 would amplify the signals as necessary, possibly convert analog signals to digital format, might provide data compression and a sequencing function or may provide two or more subcarrier frequencies to carry data into its output 19 so that a multiplicity of signals could then be separately discerned. The line 19 is the input to the telemetry system 20 whose purpose is to send data by means of the output lines 21a, 21b and 21c to a receiving module such as 14 of FIG. 1. The telemetry system can send data to a remote receiving module by the output line 21a to a telemetry antenna 22 which communicates by electromagnetic waves, or by output line 21b connected to a surface electrode conductor 23a which sends electrical signals through the body. This can be accomplished because the body is an electrical conductor. Data can also be transmitted by output line 21c which goes to an acoustic transducer 24 that generates an acoustic wave output 25 which is communicated through the body as a sonar wave is communicated through the ocean.

The output frequency of the telemetry system 20 might be in the region of 10 to 50 kHz so that electromagnetic, electrical or acoustical waves within the body are not significantly attenuated. The telemetry antenna 22 could be a coil of very thin gauge wire, e.g. No. 36 AWG, consisting of several hundred turns having an area that is as large as possible within the physical confines of the module 13b.

Putting an electrical signal in the body could be accomplished by a surface electrode element 23 comprised of a surface electrode conductor 23a which is electrically insulated, by a ceramic insulator 23b, from an electrically conducting case 23c containing module 13b. An electrical voltage between conductors 23a and 23c would be transmitted through the body as though the body was an electric wire, or more precisely, as though the body was a salt-water bath. Preferably, both the conductor 23a and the conducting surface 23c of module unit 13b would be of pure titanium or one of several titanium alloys that are known to be body compatible.

The acoustic transducer 24 might be one of a variety piezoceramics such as barium titanate. Further, in FIG. 2, a power source 26 might be a rechargeable or a replaceable battery with an associated d-c to d-c converter or d-c to a-c inverter if either the converter or inverter is necessary. The power source 26 would provide the electrical voltages and currents as necessary to power each of the electrical loads of the components of module 13. Furthermore, a timing and frequency source 27 would typically be a crystal oscillator with frequency dividers or multipliers as necessary for providing timing and frequency signals for the electrical components of module 13.

Figure 3:
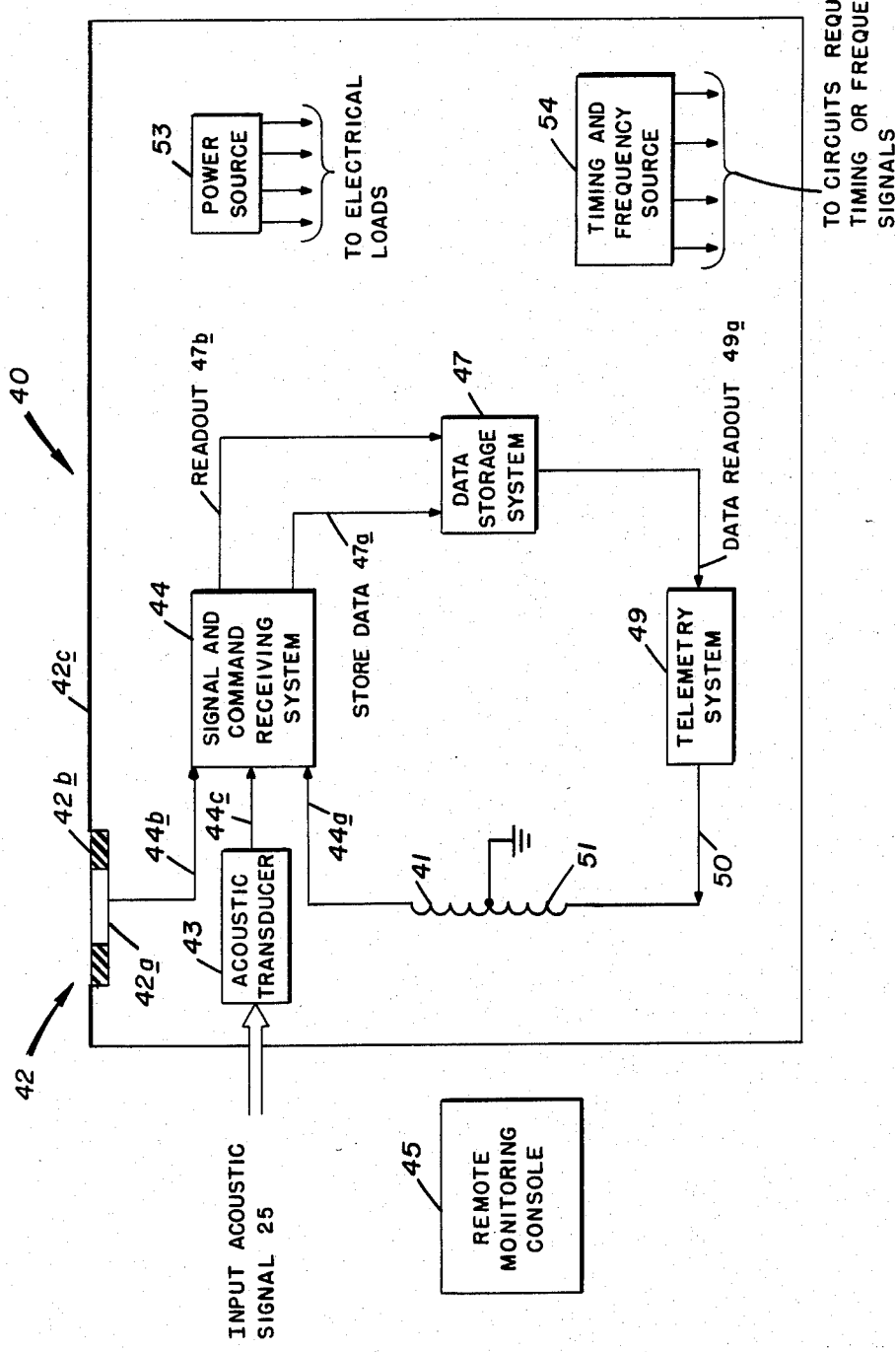
FIG. 3 is a block diagram of a typical module for receiving the acoustic, electrical, and/or electromagnetic signal transmitted by the module of FIG. 2.

In FIG. 3 is shown a typical receiving module 40. Electromagnetic signals would be detected by a receiving antenna 41 which is similar in construction to telemetry antenna 22 of FIG. 2. An electrical signal would be received by a surface electrode 42 having a surface electrode conductor 42a insulated by 42b from the electrically conducting outercase 42c of receiving module 40. An acoustic wave 25 would be converted to an electrical signal by an acoustic transducer 43. A signal and command receiving system 44 would receive inputs from lines 44a, 44b and 44c which are the output lines of the receiving antenna 41, the surface electrode 42, and the acoustic transducer 43 respectively.

In addition to receiving data by electromagnetic waves from a remote transmitting module 13, the receiving antenna 41 could receive signals from a remote monitoring console 45 the purpose of which signal is to initiate the readout of data that would be stored in the data storage system 47 of module 40. Thus, one input line to 47, from receiving system 44 is the STORE DATA line 47a, but another is a READOUT DATA line 47b which is used to cause data to be transmitted from the telemetry system 49 to the remote monitoring console 45, when such data is requested. Thus, the remote monitoring console 45 would have the capability of two-way communication with the module 40 and would typically be able to readout, store and display data that was originally stored in the data storage system 47. Although the remote monitoring console 45 might communicate by electromagnetic means, it might also directly plug into the module 40 for reading out of stored data, or it might communicate by acoustic signals.

Returning now to FIG. 3, the data storage system 47 has an output line 49a which serves as a DATA READOUT input line for the telemetry system 49. An output line 50 from the telemetry system 49 feeds into a telemetry antenna 51 which would radiate the data by electromagnetic waves to the remote monitoring console 45.

Further in FIG. 3, a power source 53 might be a rechargeable or a replaceable battery with an associated d-c to d-c converter or d-c to a-c inverter if either the converter or inverter is necessary. The power source 53 would provide the electrical voltages and currents as necessary to power each of the electrical loads of the components of module 40. Furthermore, a timing and frequency source 54 would typically by a crystal oscillator with frequency dividers or multipliers as necessary for operating the electrical components of module 40.

Figure 4:
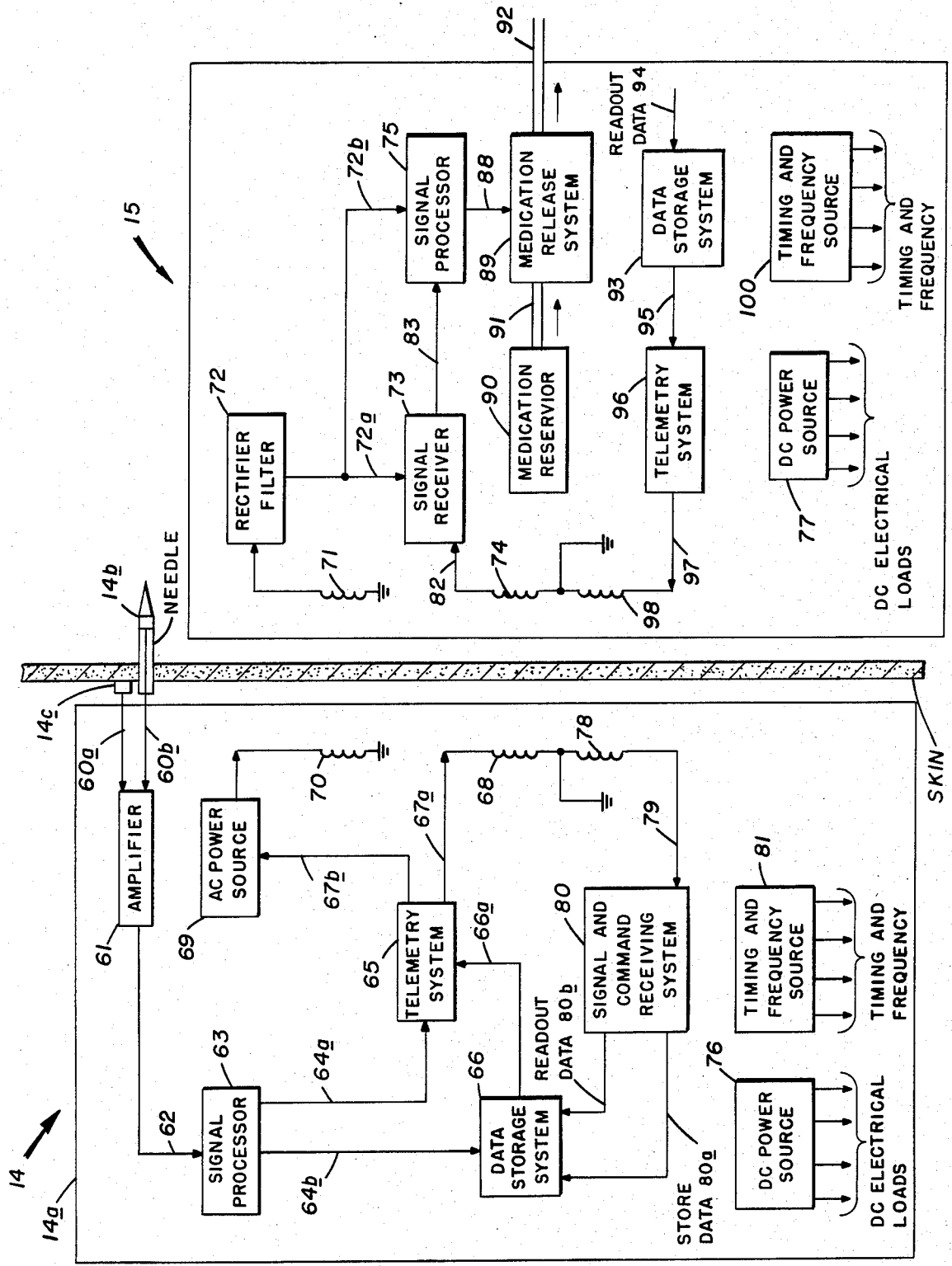
FIG. 4 is a block diagram illustrating a pair of typical intracorporeal and extracorporeal modules which communicate by means of an electromagnetic communication link.

In FIG. 4 is shown the details of an extracorporeal module 14 (of FIG. 1) which can communicate with the intracorporeal module 15, (FIG. 1) by means of an array of telemetry (i.e. transmitting) antennas and receiving antennas. The extracorporeal module 14 has: (a) a main body 14a that is external to the skin but attached to the body; (b) an implantable physiologic sensor 14b (which might be a glucose sensor on the tip of a needle); or (c) a skin mounted physiologic sensor 14c (which might be an ECG electrode) interconnected by electrical wires to the main body 14a of the extracorporeal module 14.

An amplifier 61 would have input lines 60a and 60b respectively from sensors 14b and 14c and would output by line 62 into a signal processor 63. The signal processor 63 might perform analog-to-digital conversion, data compression, data editing, signal sequencing or a variety of other signal processing operations that are well known in that art. The output lines 64a and 64b are, respectively, inputs into a telemetry system 65 and a data storage system 66. The telemetry system 65 has an output line 67a into a telemetry antenna 68 which might typically be a coil of several hundred turns of fine wire with the largest possible area within the confines of the case 14a of the module 14.

Signals emanating from the telemetry antenna 68 could be sent to a receiving antenna in the proximate intracorporeal module 15 (to be described hereinafter) to provide an input signal that has a one-to-one relationship with the output of the physiologic sensor 14b or 14c. The signal that is transmitted could be a series of digital bits with, for example a "0" corresponding to a 25 ms burst of a 49 kHz signal and a "1" corresponding to a 25 ms burst of a 51 kHz signal. There are, however, well known in the communication art, a large variety of amplitude, frequency, phase or other modulation techniques that would be successfully used to telemeter data from module 14 to module 15 as well as telemetry of data from module 15 to module 14.

Another output 67b of telemetry system 65 is an input which turns on an a-c power source 69 that causes a high intensity alternating magnetic field to emanate from the transmitting coil 70. This alternating magnetic field (typically at 25 kHz) would produce a voltage in a pick-up coil 71 contained in receiver module 15 which would be rectified and smoothed by the rectifier filter 72 which would then provide d-c power on line 72a to turn on the signal receiver 73 so that it could receive signal from the telemetry antenna 68 of module 14, via antenna 74, and furthermore to power lines such as line 72b to power a signal processor 75. In this way, many of the electrical subsystems of module 15 would be turned on only when it was desired to communicate with the extracorporeal module 14. Module 14 contains a d-c power source 76 which could be easily replaced; whereas, the d-c power source 77 of the intracorporeal module 15 could not be replaced without surgical removal, and therefore it would greatly conserve electrical power in module 15 to have much of the power to operate module 15 originate in module 14 and enter module 15 by an alternating magnetic field into the pick-up coil 71. For example, lines 72a and 72b as well as lines to other electrical circuitry of module 15, might be powered only from such an impressed alternating magnetic field energy source. A remote monitoring console (such as 45 of FIG. 3) could be used in the same manner as module 14 to provide electrical power to module 15, particularly for the purpose of receiving telemetry from data stored in module 15.

Now returning to module 14 of FIG. 4, in addition to data originating from the sensors 14b and 14c, the data storage system 66 also receives the stored data originating from the intracorporeal module 15; such data from module 15 being sent by telemetry into a receiving antenna 78 (within module 14) which is coupled by line 79 into a signal and command receiving system 80 and applied over a STORE DATA line 80a into the data storage system 66, where such data would be retained until it would be read out by the remote monitoring console such as console 45 of FIG. 3.

To read out data stored in the data storage system 66, a remote monitoring console would send a command which would be picked up by the receiving antenna 78, which antenna could typically be similar in construction to the telemetry antenna 68 that has been previously described. A command to read out data would enter the data storage system 66 on its READOUT DATA input line 80b and the data would then be read out on output line 66a. A signal would then be generated by the telemetry system 65 and be fed, over line 67a, into the telemetry antenna 68 which would then radiate the signal to a remote monitoring console such as console 45 of FIG. 3.

The d-c power supply 76, consisting of a replaceable or rechargeable cell, provides electrical power possibly by means of d-c to d-c conversion to the various electrical loads of module 14, including the a-c power source 69. The energy storage for the d-c power source 76 might be a replaceable mercury or lithium cell or a rechargeable nickel-cadmium cell. The time and frequency source 81 would be of the type described for use in module 40 of FIG. 3 and would serve the same purposes.

Returning now to a description of the intracorporeal module 15 of FIG. 4, signals received by the receiving antenna 74 would go by line 82 into the signal receiver 73 and then would be outputted on line 83 into signal processor 75. The output of the signal processor 75 is applied by line 88 to a medication release system 89.

The medication release system 89 would control release of medication that is stored in the medication reservoir 90 and that passes through a reservoir output tube 91 (through the medication release system 89) to an exit port 92 which would typically be connected to a medication catheter (not shown) that delivers medication into the body at a dosage rate dependent on the readings of the physiologic sensor, such as 14b or 14c of module 14, in a closed-loop manner.

As an example of how this might be constructively used, let us consider the case of the system shown in FIG. 4 for the treatment of diabetes. For this case, the implantable physiologic sensor 14b is a glucose sensor on the tip of a needle buried just beneath the skin and the medication reservoir contains a concentrated solution of insulin, such as U500. The sensor 14b would sense the glucose level in the human tissue and would provide an output voltage that is proportional to that level. For example, 5 millivolts would correspond to a full-scale of 500 mg of glucose per deciliter of blood. The timing and frequency source 81 (of module 14) originates a timing signal that would cause a measurement to be made for 100 ms duration every 10 minutes. When a measurement is made, the signal processor 63 converts the signal out of amplifier 61 into a series of 8 digital bits that corresponds to the voltage output of sensor 14b. Then, for an additional 500 ms (each 10 minute time period), the telemetry system 65 and the a-c power source 69 are each turned on so as to transmit the data in digital form into module 15. The signal processor 75, of module 15, compares the value corresponding to the 8 bits with a previous value stored in a memory position of signal processor 75 and then causes the medication release system 89 to increase, decrease or maintain constant the flow rate of insulin.

To continue the description of module 15, a data storage system 93 would store data from various electrical and fluid measurements within the module 15. Upon command from an external source, such as module 14, that enters line 94 as a READOUT DATA command, the stored data would be read out by the telemetry system 96 through line 97 into the telemetry antenna 98 and thence into the receiving antenna 78 of module 14, eventually residing within the data storage system 66 of the extracorporeal module 14.

By this method, the extracorporeal module 14 can be used to store data collected from the intracorporeal module 15, thus minimizing the size of the data storage system within module 15 and further minimizing the amount of electrical power required to operate module 15, which module can only be replaced by surgical intervention. This technique has the advantage of minimizing the size and cost of the typically expensive intracorporeal module 15, while at the same time extending its useful life thus extending the time period between surgical replacements.

The d-c power source 77 and the timing and frequency source 100 of module 15 are of similar construction and serve the same functions respectively as the d-c power source 76 and timing and frequency source 81 of module 14. The only exception would be that the d-c power source 77 would preferably include a lithium cell energy storage means which provides the highest energy density and longest life for an implanted device without the need for recharging.

Various other modifications, adaptations and alternations are of course possible in light of the above teachings. Therefore, it should be understood at this time that within the scope of the appended claims the invention may be practiced otherwise than as specifically described.

What is claimed is:

1. A medication delivery system for delivering medication into a patient, said medication delivery system comprising:
    a sensor module including,
        a sensor module housing adapted to be externally mounted on a patient's skin,
        a needle adapted to be buried just beneath said patient's skin;
        a glucose sensor physically connected to the tip of said needle,
        a telemetry means mounted in said sensor module housing and electrically connected to said glucose sensor, for transmitting a signal carrying sensed glucose level information; and
    a medication release module adapted to be implanted in said patient for dispensing medication into said patient, including,
        a medication release module housing adapted to be implanted in said patient, a receiver means mounted in said medication release module housing for receiving signals transmitted by said telemetry means and for decoding sensed glucose level information, a delivery means mounted in said housing and connected to said receiver means for causing medication to be delivered into said patient in accordance with said sensed glucose level information.

2. The apparatus of claims 1 wherein, said needle is replaceably connected to said housing.

3. The apparatus of claims 1 wherein, said telemetry means further comprising:

a processing means connected to said glucose sensor for generating binary data corresponding to sensed glucose levels; and a telemetry transmitted connected to said processing means for transmitting a signal carrying said binary data.

4. The apparatus of claim 3 wherein said medication release module further includes a means for gathering and storing operational data and a transmitting means for transmitting a signal carrying said operational data, and wherein said sensor module further includes a telemetry receiver means for receiving said signal transmitted by said transmitting means, and a storage means connected to said telemetry receiver means for storing the received operational data.

5. The apparatus of claim 3 wherein said receiver means detects said signal carrying said binary data and wherein said delivery means includes:

a memory means operably connected to said receiver means for storing said binary data, and a signal processing means, operably coupled to said receiver means and said memory means, for comparing the most recently received binary data with values previously stored in memory for causing said medication release modules to correspondingly alter the medication delivery rate.

6. The apparatus of claim 1 wherein the frequency of said signal is proportional to the level of blood sugar.

* * * * *